(12) United States Patent
Pade

(10) Patent No.: US 6,636,051 B2
(45) Date of Patent: Oct. 21, 2003

(54) WIRING HARNESS PLUG, ESPECIALLY AS PLANAR TWO-CELL LIMITING CURRENT PROBE HAVING AN INJECTION-MOLDED COVER ELEMENT

(75) Inventor: Wolfgang Pade, Illingen (DE)

(73) Assignee: Robert Bosch GmbH, Stuttgart (DE)

( * ) Notice: Subject to any disclaimer, the term of this patent is extended or adjusted under 35 U.S.C. 154(b) by 0 days.

(21) Appl. No.: 10/004,937

(22) Filed: Dec. 3, 2001

(65) Prior Publication Data

US 2002/0111049 A1 Aug. 15, 2002

(30) Foreign Application Priority Data

Dec. 1, 2000 (DE) ..................................... 200 20 373 U

(51) Int. Cl.$^7$ ............................................... H01H 31/04
(52) U.S. Cl. ...................................... 324/538; 324/538
(58) Field of Search .................................. 324/149, 538, 324/539, 156; 439/43, 617, 668; 156/49, 51; 425/110; 385/15, 76, 94, 95, 101, 129; 73/23.31, 28.01

(56) References Cited

U.S. PATENT DOCUMENTS

| | | | | |
|---|---|---|---|---|
| 5,435,735 A | * | 7/1995 | Wittig et al. | 439/492 |
| 6,032,514 A | * | 3/2000 | Weyl et al. | 73/31.05 |
| 6,132,256 A | * | 10/2000 | Morsdorf et al. | 439/620 |
| 6,422,766 B1 | * | 7/2002 | Althaus et al. | 385/94 |
| 6,478,906 B1 | * | 11/2002 | Azdasht et al. | 156/73.1 |

* cited by examiner

Primary Examiner—N. Le
Assistant Examiner—Amy He
(74) Attorney, Agent, or Firm—Kenyon & Kenyon

(57) ABSTRACT

For the adjustment of planar broad-band lambda probes, direct access is obtained to an adjustment element made of a resistor layer applied to a ceramic substrate. For this purpose a corresponding cover element is removed from the probe, or rather, from the probe developed as a wiring harness plug. A cover element is formed directly with the remaining part of wiring harness plug, preferably connected as one piece, and the cover element is made transparent in such a way that a laser beam can penetrate cover element, and processing can occur at adjustment element, even when cover element has already been mounted on wiring harness plug.

7 Claims, 1 Drawing Sheet

WIRING HARNESS PLUG, ESPECIALLY AS PLANAR TWO-CELL LIMITING CURRENT PROBE HAVING AN INJECTION-MOLDED COVER ELEMENT

FIELD OF THE INVENTION

The present invention relates to a wiring harness plug, especially a planar two-cell limiting current probe, including a housing made of a base element and a cover element, as well as a sensor unit and an adjusting element connected to the sensor unit.

BACKGROUND INFORMATION

Wiring harness plugs of the above kind are, as a rule, developed as lambda probes, the terminals provided in the wiring harness plug being provided for adjustment, signaling and heating of the probe. Lambda probes and lambda closed loop A/F control, these days, represent an effective exhaust gas cleaning method in conjunction with a three-way catalyst. The lambda probe, which is, for example, screwed into an exhaust gas system, includes a measuring sensor for determining the oxygen content in the exhaust gas.

Residual oxygen content is very suitable as a measured variable, and regulates the air/fuel ratio, since it indicates precisely whether the air/fuel mixture is combusting completely.

In this regard, the lambda probe delivers a voltage signal which represents the momentary value of the mixture's composition and follows the changes in the mixture. Fuel supply to the engine is regulated, corresponding to the signal of the lambda probe, by a carburetion device in such a way that a stoichiometric air/fuel ratio lambda=1 is reached. Heated or unheated probes are installed, depending on the construction of the exhaust gas system and the installation conditions. Lambda probes find further application outside motor fuel vehicles, for instance, for regulating gas engines or oil/gas burners.

In particular, broad-band lambda probes are constructed in a modular way, and permit the integration of several functions, in connection with planar technique. As a rule, they have functional layers made of a porous protective layer, an outer electrode, a sensor foil, an inner electrode, a reference air channel foil, an insulating layer, a heater, a heating foil and terminal contacts.

Since the broad-band lambda probe includes the combination of a Nernst concentration cell (=sensor cell) with an oxygen ion-transporting pump cell, it can measure very accurately not only at the stoichiometric point where lambda=1, but also in the lean and the rich range.

Each probe has to be adjusted individually. For this, the probe has a built-in resistor ("mini-hybrid"). The adjustment, which is preferably made with the aid of a laser beam, is done in such a way that the resistor layer, which is on a ceramic substrate, is correspondingly removed, whereby a change in resistance is brought on, resulting in an adjustment.

Up to now, the adjustment has taken place in that the housing of the wiring harness plug, in which the resistor is built in, is brought to the adjustment location without the cover element. After the appropriate laser treatment for the adjustment, the cover element is then slipped on.

The cover element has additional seals, in order to prevent humidity, dirt or the like from penetrating the wiring harness plug.

One disadvantage of the design of the wiring harness plug described above is that additional working and installation steps are required in order to close the wiring harness plug appropriately for its function after the adjustment. Additionally an additional cover element is separately manufactured together with a seal, and this element is made available in the adjustment region.

SUMMARY OF THE INVENTION

An object of the present invention is to further develop a specific embodiment of a wiring harness plug having hybrid electronics so that it is adjustable in a simple manner.

The object is attained in that the cover element is undetachably positioned on the housing, and that the cover element is transparent, so that a laser beam can penetrate the cover element and processing of the adjustment element can take place.

An advantage of the present invention is that the cover element is already mounted on the wiring harness plug before the adjustment. Preferably, the cover element is positioned directly and undetachably on the housing, such as being extruded on the housing. This makes it no longer necessary to produce an additional component, and to make it available at the location of the adjustment, and mounting it.

This also does away with seals liable to aging, which have been used to seal the cover element from the housing in designs up to now.

Preferably elements are provided in the housing, into which individual parts of the probe can be installed. These elements are preferably developed as clamping elements.

A further specific embodiment of the present invention is developing the cover element and the base body in one piece.

Further advantageous refinements of the present invention come to light from the following description, the claims, as well as the drawings.

DETAILED DESCRIPTION

Figure 1:
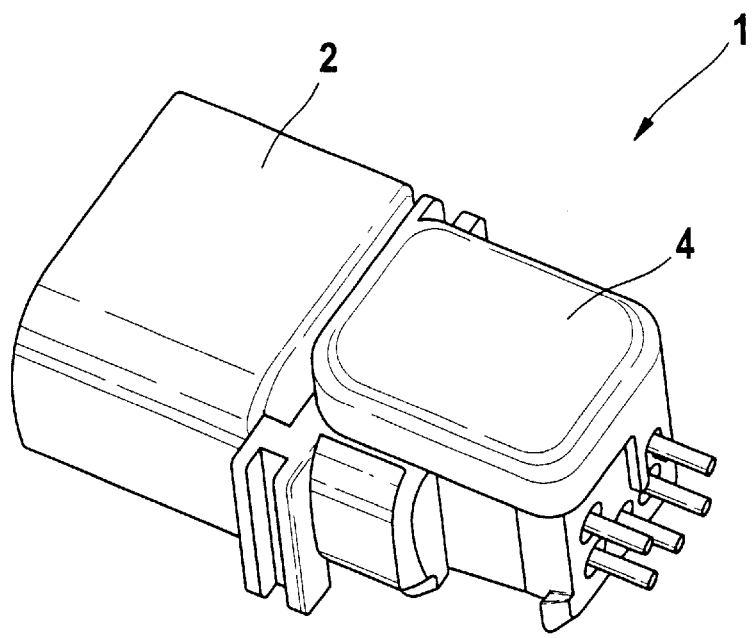
FIG. 1 shows a perspective view of the wiring harness plug according to the present invention.
Figure 2:
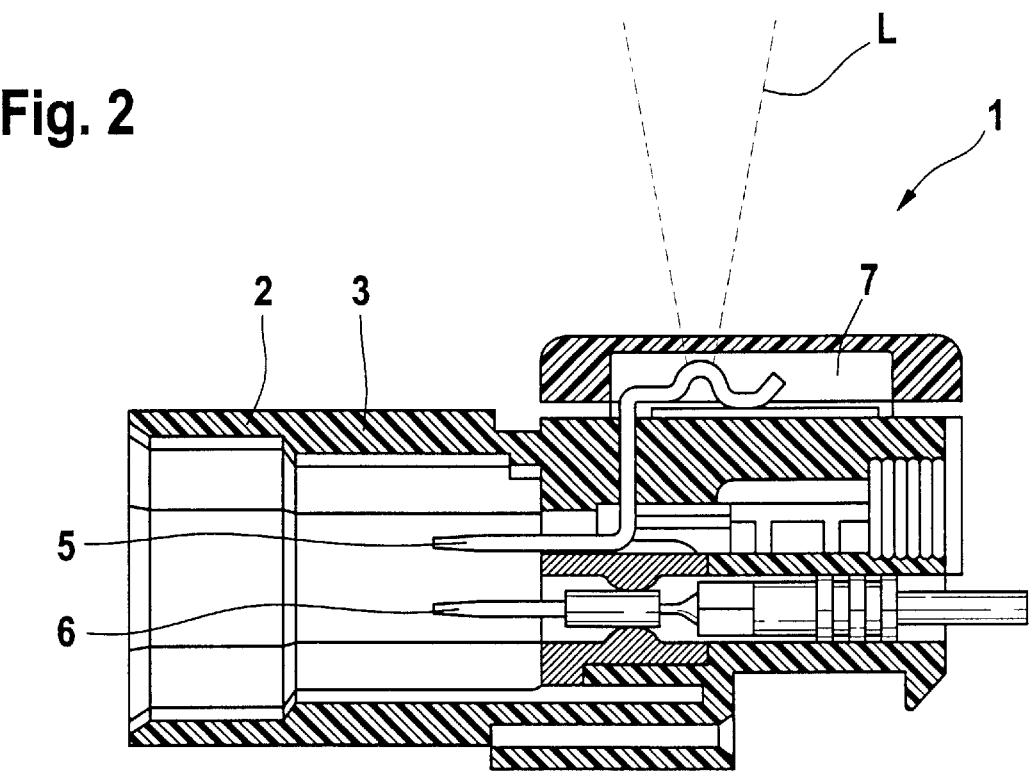
FIG. 2 shows a cross section through the wiring harness plug as in FIG. 1.

Wiring harness plug 1, as shown in FIGS. 1 and 2, includes one housing 2, which, in turn, is made of one base body 3 and a cover element 4.

Furthermore, inside housing 2, insertion parts 5 are positioned, which form the sensor unit which, for example, is equivalent to a two-cell limiting current probe.

Inside housing 2, plug contacts 6 are positioned as a part of insertion parts 5, which, in turn, form a part of the sensor unit.

Alternatively to this, it can be provided that any kind of lambda probes, that is, also planar broad-band lambda probes can be used.

Especially the planar broad-band lambda sensor unit illustrated in FIG. 2 has to be adjusted directly after installation. For this purpose, the sensor unit has an adjustment element 7 made of a resistor layer made of a ceramic substrate (not shown in greater detail in the drawing).

It is provided, according to the present invention, that wiring harness plug 1, provided with insertion parts 5, be closed up immediately after its installation. Cover element 4 is preferably formed as one piece with housing 2, by the cover element being extruded on housing 2.

The aim of extruding cover element 4 on housing 2 is to replace the seal known per se from the related art, by making a hermetic seal of adjusting element 7 and thereby of the sensor unit.

The required adjustment of adjusting element 7 is made after the installation.

For the adjustment, cover element 4 is formed in such a way that it can be penetrated by laser beam L almost free of absorption, so that the processing of adjustment element 7 can be done even with cover element 4 already mounted.

Based on cover element 4 being made transparent to the laser beam L selected, it has become possible to produce especially planar broad-band lambda probes completely, even before their adjustment, and to seal them hermetically, so that no further processing has to be done after the adjustment.

What is claimed is:

1. A wiring harness plug, comprising:
   a housing including a base body and a cover element;
   a sensor element; and
   an adjustment element connected to the sensor element, wherein:
      the cover element is undetachably positioned on the housing,
      the cover element is transparent, so that a laser beam can penetrate the cover element and processing can take place at the adjustment element, and
      the adjustment element is configured to be adjusted by the laser beam received through the cover element.

2. The wiring harness plug according to claim 1, wherein:
   the wiring harness plug corresponds to a planar two-cell limiting current probe.

3. The wiring harness plug according to claim 1, wherein:
   the cover element is made of plastic and is extruded on the housing to form one piece with the housing.

4. The wiring harness plug according to claim 1, wherein:
   the cover element demonstrates one of no absorption and only a low degree of absorption with respect to a wavelength of the laser beam.

5. The wiring harness plug according to claim 1, further comprising:
   elements for accommodating insertion parts that can be inserted into the wiring harness plug.

6. The wiring harness plug according to claim 5, wherein:
   the elements include clamping elements.

7. The wiring harness plug according to claim 1, wherein the adjustment element is made of a resistor layer.

* * * * *